United States Patent [19]

Hörrmann

[11] Patent Number: 4,505,933
[45] Date of Patent: Mar. 19, 1985

[54] FATTY ALDEHYDES IN THE TREATMENT OF MULTIPLE SCLEROSIS

[76] Inventor: Wilhelm Hörrmann, Obb, Fed. Rep. of Germany

[21] Appl. No.: 470,970

[22] Filed: Mar. 1, 1983

Related U.S. Application Data

[63] Continuation-in-part of Ser. No. 303,634, Feb. 1, 1982, abandoned, which is a continuation-in-part of Ser. No. 127,817, Mar. 6, 1980, abandoned, which is a continuation-in-part of Ser. No. 787,902, Apr. 15, 1977, abandoned, which is a continuation-in-part of Ser. No. 652,309, May 3, 1976, abandoned, which is a continuation-in-part of Ser. No. 600,375, Jul. 30, 1975, abandoned, which is a continuation-in-part of Ser. No. 450,458, Mar. 12, 1974, abandoned, which is a continuation-in-part of Ser. No. 274,754, Jul. 24, 1972, abandoned, which is a continuation-in-part of Ser. No. 805,934, Feb. 12, 1969, abandoned, which is a continuation-in-part of Ser. No. 634,884, May 1, 1967, abandoned, which is a continuation-in-part of Ser. No. 412,862, Nov. 20, 1964, abandoned, which is a continuation-in-part of Ser. No. 211,827, Jul. 23, 1962, abandoned, which is a continuation-in-part of Ser. No. 824,798, Jul. 3, 1959, abandoned, which is a continuation-in-part of Ser. No. 029,850, Apr. 18, 1959, abandoned, which is a continuation-in-part of Ser. No. 907,343, May 18, 1958, abandoned.

[51] Int. Cl.$^3$ .............................................. A61K 31/12
[52] U.S. Cl. .................................. 514/693; 514/703; 514/723
[58] Field of Search ........................................ 424/331

[56] References Cited

PUBLICATIONS

Chem. Abst. (1), 49-5299ef, and 5289f, (1955).
Chem. Abst. (2), 43-1580i, (1949).
Chem. Abst. (3), 31-15067, (1937).
Chem. Abst. (4), 40-1449, and 56977 (1949).

*Primary Examiner*—Stanley J. Friedman

[57] ABSTRACT

This application relates to the administering of fatty aldehydes (and acids) to patients suffering from Multiple Sclerosis, for therapeutic purposes.

1 Claim, No Drawings

FATTY ALDEHYDES IN THE TREATMENT OF MULTIPLE SCLEROSIS

This application is a continuation in part of Ser. No. 303,634 filed Feb. 1, 1982, which is continuation-in-part of Ser. No. 127,817, filed Mar. 6, 1980, which is continuation-in-part of Ser. No. 029,850, filed Apr. 18, 1959, which is a continuation-in-part of Ser. No. 907,343, filed May 18, 1958, which is a continuation-in-part of Ser. No. 787,902, filed Apr. 15, 1977, which is a continuation-in-part of Ser. No. 652,309, filed May 3, 1976, which is a continuation-in-part of Ser. No. 600,375, filed July 30, 1975, which is a continuation-in-part of Ser. No. 450,458, filed Mar. 12, 1974, which is a continuation-in-part of Ser. No. 274,754, filed July 24, 1972, which is a continuation-in-part of Ser. No. 805,934, filed Feb. 12, 1969, which is a continuation-in-part of Ser. No. 634,884, filed May 1, 1967, which is a continuation-in-part of Ser. No. 412,862, filed Nov. 20, 1964, which is a continuation-in-part of Ser. No. 211,827, filed July 23, 1962, which is a continuation-in-part of Ser. No. 824,798, filed July 3, 1959 all are abandoned.

INTRODUCTION

Multiple Sclerosis is a widespread and severe disease of the central nervous system. The patients are first affected mostly in their twenties or thirties. The disease is nearly always progressive, interrupted only by temporary remissions. Pathological alterations in the white substance of the nervous system is followed by impairment of eyesight, ataxia, tremor, paralysis and other neuological disorders. After years or decades of suffering the disease usually results in invalidity or death.

Many efforts of the medical sciences to explore the cause of the disease have failed so far.

It is the subject of this invention that Multiple Sclerosis is caused by a structural deficiency in the bodies own plasmalogen, fatty aldehyd and fatty acids system which is the basis for inflammatory processes leading to sclerotic focuses within the central nervous system, and that a substitution therapy is therefor indicated.

CHEMISTRY

The compounds of the invention are aliphatic unsaturated compounds. They are unbranched. They are fatty acids and aldehydes. Structural formulae for the compounds are set forth below. The geometric isomers are indicated by "cis" and "trans" notation, and the optical isomers are indicated by and notation.

Structural Formulas of the substances

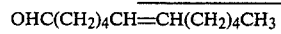 (1)
cis

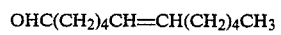 (2)
trans

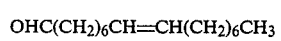 (3)
cis

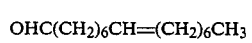 (4)
trans

 (5)
cis

-continued
Structural Formulas of the substances

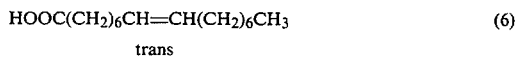 (6)
trans

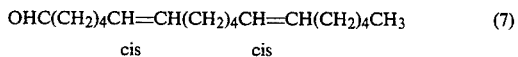 (7)
cis        cis

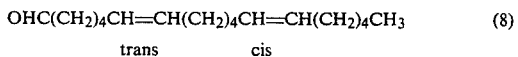 (8)
trans      cis

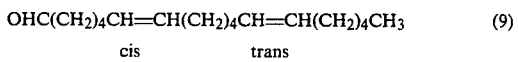 (9)
cis        trans

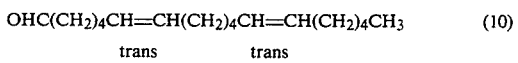 (10)
trans      trans

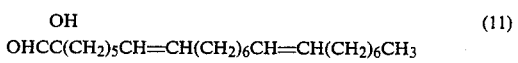 (11)
alpha   cis        cis

 (12)
alpha   trans      cis

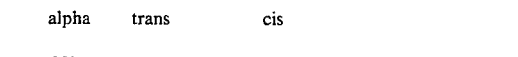 (13)
alpha   cis        trans

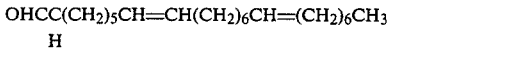 (14)
alpha   trans      trans

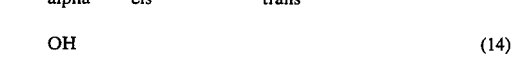 (15)
beta    cis        cis

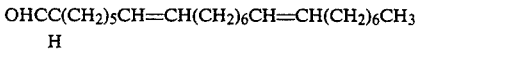 (16)
beta    trans      cis

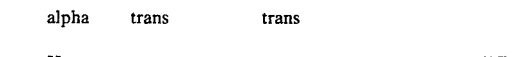 (17)
beta    cis        trans

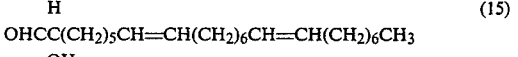 (18)
beta    trans      trans

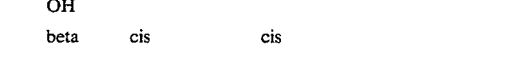 (19)
alpha   cis        cis

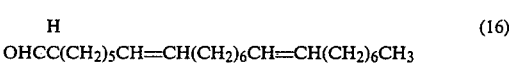 (20)
alpha   cis        trans

-continued
Structural Formulas of the substances $$HOOCC(CH_2)_5\overset{OH}{\underset{H}{C}}H=CH(CH_2)_6CH=CH(CH_2)_6CH_3 \quad (21)$$
alpha     trans     cis $$HOOCC(CH_2)_5\overset{OH}{\underset{H}{C}}H=CH(CH_2)_6CH=CH(CH_2)_6CH_3 \quad (22)$$
alpha     trans     trans $$HOOCC(CH_2)_5\overset{H}{\underset{OH}{C}}H=CH(CH_2)_6CH=CH(CH_2)_6CH_3 \quad (23)$$
beta     cis     cis $$HOOCC(CH_2)_5\overset{H}{\underset{OH}{C}}H=CH(CH_2)_6CH=CH(CH_2)_6CH_3 \quad (24)$$
beta     cis     trans $$HOOCC(CH_2)_5\overset{H}{\underset{OH}{C}}H=CH(CH_2)_6CH=CH(CH_2)_6CH_3 \quad (25)$$
beta     trans     cis $$HOOCC(CH_2)_5\overset{H}{\underset{OH}{C}}H=CH(CH_2)_6CH=CH(CH_2)_6CH_3 \quad (26)$$
beta     trans     trans

DERIVATIVES OF THE ALDEHYDES

Aldehydes occur in 2 different modifications:
1. in onolic form

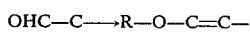

wherein R is H or C
2. in hydrated form

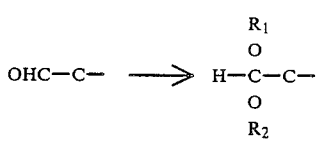

wherein $R_1$ and $R_2$ are identical or different and are H or C.

Typical examples are the ethers of ethanol glycol, glycerol and the esters of acetic acid, opcal acid and which form noncylic or cyclic structures

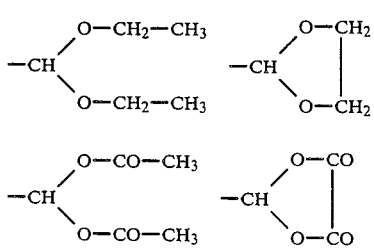

DERIVATIVES OF THE ACIDS

Derivatives of the acids are the salts and the esters. Typical examples are the sodium (Na) salts and the ethanol and glycerol esters.

Important pharmaceutical examples for both fatty aldehydes and fatty acides are the ethers of the aldehydes and the esters of the acides with physiologic acids of bilo, namely glyco-and tauro cholic, desoxycholic, lithocholic acids or glycerol.

Physiologic derivatives of fatty aldehydes and fatty acids are the lipids especially those containing glycerol, hexoses, sphingosin, kolamin, cholin, phosphat and the like. Important derivatives of fatty aldhydes (and acids) are the plasmalogens.

How to make the invention:

The synthesis of the claimed fatty aldehydes and acids and their derivatives can be performed in different ways all well known to chemistry and biochemistry. Examples are given in the published U.S. Pat. No. 4,239,756.

How to use the invention:

It is preferred to administer the compounds in form of mixtures containing their isomers in equimolar amounts. In cases of multiple sclerosis the treatment is started with the isomers of 6-n-dodencoic aldehyde 8-n-hexadecenoic aldehyde and 8-n-hexadecenoic acid      (I)

to which in the course of 6 weeks the isomers of 6,12-n-octadecadienoic aldehyde 8,16-n-tetracosadienoic-2-hydroxy aldehyde and 8,16-n-tetracosadienoic-2hydroxy acid      (II)

may be added, if necessary.

Dosage for group I of isomers pro die 50-20 omg/kg of the mixture dosage for group II of isomers pro dies 50-20 omg/kg of the mixture.

Dosages are general mean values and may be raised, if necessary.

Dosages relate to the free compounds.

While parenteral administration should be restricted to emergency cases, the preferred way of adiministering is the oral one as compound per se or derivative combined with glycerol, bile acid, plasmalogen and the like.

The compounds may be diluted in plant oils, enclosed in capsules and mixed in emulsions.

The total dosage per day must not be given in one single dose but in several doses distributed over the day. Being a substitution therapy the administration must be continued over long periods of time.

In case group I of the isomers is given in combination with group II dosage is 100-400 mg/kg of the mixture.

I claim:

1. A method of treating multiple sclerosis in a patient having multiple sclerosis comprising administering to said patient 100-400 mg/kg daily of at least one of the geometric and optical isomers of
    6-n-dodecenoic aldehyde
    8-n-hexadecenoic aldehyde
    and 6,1 2-n-octadecadienoic aldehyde or
    8,1 6n-tetracosadienoic-2-hydroxy aldehyde
per se or as an ether of glycol, glycerol or physiologic acids of bile or in form of plasmalogen, said isomer being diluted in plant oils or in the form of capsule or emulsion.

* * * * *